United States Patent [19]

Fenyvesi et al.

[11] Patent Number: 4,547,572
[45] Date of Patent: Oct. 15, 1985

[54] CYCLODEXTRIN POLYMERS SWELLING QUICKLY AND TO A GREAT EXTENT IN WATER AND PROCESS FOR THE PREPARATION THEREOF

[75] Inventors: Éva Fenyvesi; József Szejtli; Béla Zsadon; Balázs Antal; Ildikó Wágner née Koháry, all of Budapest, Hungary

[73] Assignee: Chinoin Gyogyszer es Vegyeszeti Termekek Gyara Rt., Budapest, Hungary

[21] Appl. No.: 577,153

[22] Filed: Feb. 6, 1984

[30] Foreign Application Priority Data

Feb. 4, 1983 [HU] Hungary .................................. 387/83

[51] Int. Cl.$^4$ ............................................. C08B 37/16
[52] U.S. Cl. .................................................... 536/103
[58] Field of Search .......................................... 536/103

[56] References Cited

U.S. PATENT DOCUMENTS

| | | | |
|---|---|---|---|
| 1,908,485 | 5/1933 | Meigs ................................... | 536/103 |
| 2,698,937 | 1/1955 | Staerkle et al. ...................... | 536/103 |
| 2,845,417 | 7/1958 | Kesler et al. ......................... | 536/103 |
| 3,472,835 | 10/1969 | Buckler et al. ...................... | 536/46 |
| 4,274,985 | 6/1981 | Szejtli et al. ........................ | 525/54.2 |

FOREIGN PATENT DOCUMENTS 1244990  9/1971  United Kingdom ................ 536/103

Primary Examiner—Ronald W. Griffin
Attorney, Agent, or Firm—Karl F. Ross; Herbert Dubno

[57] ABSTRACT

The invention relates to cyclodextrin polymers swelling quickly and to a great extent in water and a process for the preparation thereof.

The cyclodextrin polymers according to the invention contain as additive n-octanol having or glycol derivative or glycerol.

The cyclodextrin polymers according to the invention are prepared by reacting cyclodextrin and epichlorohydrin in aqueous alkaline medium. In the reaction the cyclodextrin is reacted with 10 to 20 moles of an alkali hydroxide, 10 to 20 moles of epichlorohydrin and 2 to 8 moles of an alcohol additive, n-octanol, glycol derivative or glycerol calculated on 1 mole of cyclodextrin optionally in the presence of 10 to 15 moles of an organic solvent vaporizing at the reaction temperature or 8 to 12 moles of a high boiling organic solvent assuring heterogeneous phase.

13 Claims, No Drawings

CYCLODEXTRIN POLYMERS SWELLING QUICKLY AND TO A GREAT EXTENT IN WATER AND PROCESS FOR THE PREPARATION THEREOF

The invention relates to cyclodextrin polymers swelling quickly and to a great extent in water and to a process for the preparation thereof.

The water-insoluble cyclodextrin polymers are produced by the cross-linking polymerization of cyclodextrins. Generally epichlorohydrin or diepoxy derivatives (e.g. diepoxy butane, diepoxypropyl ether, ethylene glycol diepoxypropyl ether) are used as cross-linking agents, the polymer being produced either by block polymerization (published Dutch patent application No. 6,505,361, U.S. Pat. No. 3,472,835) or as regular pearls (GB patent specification No. 1,244,990) or as foamed polymerizates having greater specific surface (Hungarian patent application No. 1188/81). The mechanical properties of the rigid materials improve significantly by incorporating polyvinyl alcohol (U.S. Pat. No. 4,274,985) and this is important while using them as stationary phase in column chromatography.

The water-absorbing capacity of the known cyclodextrin polymers may be changed within broad limits by known methods, i.e. by changing the excess of cross-linking agent and the concentration of starting cyclodextrin. The water-absorbing capacity of the product is greater when a greater excess of cross-linking agent is used or the cross-linking process is performed in more diluted cyclodextrin solutions. Thus cyclodextrin polymers having greater water-absorbing capacity are obtained which adsorb the water. However, absorption is slow and in certain cases even hours are needed for achieving the total swelling. The cyclodextrin polymers which are prepared by the known processes and show quick swelling, have small water-absorbing capacity, when the product shows, however, great water-absorbing capacity, the rate of the water-absorption is low. Consequently, polymers, which adsorb great quantity of water quickly, cannot be produced by the known processes.

The object of the present invention is to provide a process by which quickly swelling cyclodextrin polymers having great water-absorbing capacity may be produced.

It was surprisingly found that cyclodextrin polymers fulfilling the above requirements may be obtained when according to the invention cyclodextrin and epichlorohydrin are reacted in aqueous alkaline medium using 10 to 20 moles of an alkali hydroxide and 10 to 20 moles of epichlorohydrin as well as 2 to 8 moles of an alcohol additive, that is an alcohol having 2 to 8 carbon atoms or glycol derivative or glycerol and optionally 10 to 15 moles of an organic solvent vaporizing at the reaction temperature, preferably dichloro ethane or 8 to 12 moles of a high boiling organic solvent assuring heterogeneous phase, preferably toluene calculated per 1 mole of the cyclodextrin.

According to the invention α-, β- or γ-cyclodextrin or the mixture thereof may be used as the cyclodextrin. The type of the cyclodextrin does not influence significantly the swelling capacity of the product obtained.

The process of the invention is performed in an aqueous alkaline medium. The alkaline reaction of the reaction mixture is achieved by using alkali hydroxides.

The polymer having advantageous properties may be obtained by the process of the invention since the alcohol additive (alcohol having 2 to 8 carbon atoms, glycol derivative or glycerol) is incorporated into the polymer structure on the effect of the epichlorohydrin and so practically loosens the polymer structure thereby influencing favorably both the water-absorbing and the swelling capacity of the polymer. This effect is unexpected and surprising since the polymers according to the Hungarian patent specification No. 177,419, into which polyvinyl alcohol is incorporated, do not show greater water-absorbing or swelling capacity then the polymers without polyvinyl alcohol, only their mechanical strength is greater.

In the process according to the invention the alcohol additives, which may be used, are alcohols having 2 to 8 carbon atoms and glycol derivatives, e.g. ethanol, propanol, butanol, pentanol, hexanol, heptanol, octanol, ethylene glycol, propylene glycol, butylene glycol and other glycols both in form of normal and straight branched isomers. Triethylene glycol, tetraethylene glycol and glycerol may also be used.

The polymerization reaction according to the invention is performed preferably at a temperature of from 60° to 80° C., but lower or higher temperatures may also be applied.

When products having a foamed structure are to be produced, a foaming agent, e.g. a solvent boiling at the reaction temperature (e.g. dichloro ethane) is also introduced into the reaction mixture. When pearl polymerizates should be obtained, a water-immiscible solvent having a higher boiling point, preferably toluene is added to the reaction mixture.

The polymers according to the invention swell in water quickly and to a great extent and may be applied advantageously as disintegrating agents for preparing tablets (see Table IV).

Further details of the invention are shown by the following Examples without limiting the scope of the invention thereto.

EXAMPLE 1

In 10 ml of water of 60° C. 3.0 g (75 mmoles) of sodium hydroxide, then 5.0 g (4.4 mmoles) of β-cyclodextrin are dissolved. To the reaction mixture 2.5 ml (2.8 g, 14.5 mmoles) of tetraethylene glycol are mixed. Thereafter 5.7 ml (6.7 g, 72.7 mmoles) of epichlorohydrin are added during about 1.5 hours at 60° C. After cooling the gel obtained is washed saltfree with distilled water, dehydrated with acetone, dried at 105° C. and pulverized. 6.8 g of white powdery material (product A) are obtained which has a cyclodextrin content of 50.6% determined by iodometry.

Cyclodextrin polymer having the same water-absorbing capacity is produced by the known manner without an alcohol additive in the following way. In 10 ml of water of 60° C. 2.2 g (55 mmoles) of sodium hydroxide, then 5.0 g (4.4 mmoles) of β-cyclodextrin are dissolved. To the reaction mixture 4.2 ml (5.0 g, 54 mmoles) epichlorohydrin are added during about 1.5 hours. 5.3 g white powdery material (product B) are obtained which has a cyclodextrin content of 53.4%.

EXAMPLE 2

In 30 ml of water of 60° C. 4.4 g (110 mmoles) of sodium hydroxide, then 25 g (22 mmoles) of β-cyclodextrin are dissolved. To the solution so obtained 9.0 ml (10.0 g, 161 mmoles) of ethylene glycol are mixed thereafter 8.5 ml (10.0 g, 108 mmoles) of epichlorohydrin are added. The reaction mixture is maintained at 60° C. for 1 hour then 20 ml of dichloro ethane foaming agent is mixed to the reaction mixture. In the second step of the reaction the solution of 8.0 g (200 mmoles) of sodium hydroxide in 6.5 ml water and 17 ml (20.1 g, 217 mmoles) of epichlorohydrin are added and the reaction mixture is heated to 75° C. The dichloro ethane vaporizes, the system becomes foamy and solidifies. After cooling the reaction mixture obtained is washed, dried and milled as described in Example 1. So 30.5 g product (product C) are obtained having a cyclodextrin content of 54.7%.

A cyclodextrin foamed polymer having a similar water-absorbing capacity is obtained by the known manner in the following way. In 50 ml of water of 60° C. 8.8 g (220 mmoles) of sodium hydroxide and 25 g (22 mmoles) of β-cyclodextrin are dissolved thereafter 8.5 ml (10.0 g, 108 mmoles) of epichlorohydrin are added. To the reaction mixture obtained 40 ml of dichloro ethane foaming agent are mixed. In the second step of the reaction the procedure described above is repeated. So 32.0 g product (product D) are obtained which have a cyclodextrin content of 52.2%.

EXAMPLE 3

In 250 ml of water of 60° C. 75.0 g (1.88 mmoles) sodium hydroxide, then 125 g (0.11 moles) of β-cyclodextrin are dissolved. To the reaction mixture 75.0 ml (84.4 g, 0.43 moles) of tetraethylene glycol are admixed. Thereafter 90 ml (106.2 g, 1.15 moles) of epichlorohydrin are added for 1 hour whereafter 125 ml toluene and further 52.5 ml (62.0 g, 0.67 moles) epichlorohydrin are added. The reaction mixture is stirred for another 3 hours intensively while maintaining the temperature at 60° C. A solid product is obtained which consists of pearly particles. The particles are washed with water, dehydrated with 5 l of acetone and dried in a drying oven at 120° C. 160 g of product (product E) are obtained which has a cyclodextrin content of 49.0%.

In the same way but without tetraethylene glycol 144 g polymer (product F) are obtained which has a cyclodextrin content of 49.7%.

EXAMPLE 4

In 10 ml of water of 60° C. 3.0 g (75 mmoles) of sodium hydroxide, then 5.0 g (4.4 mmoles) β-cyclodextrin are dissolved. To the solution obtained one of the substances stated in Table IV is added under stirring in the quantity given. For dissolving the polyvinyl alcohol at least a further 0.5 hour stirring is needed, with additives of low molecular weight the reaction mixture can be homogenized quickly. Thereafter 3.6 ml (45.9 mmoles) of epichlorohydrin are added to the reaction mixture for 1 hour, whereafter another 2.1 ml (26.7 mmoles) of epichlorohydrin are admixed. The reaction temperature is always maintained at 60° C. The gelization occurs after 10 to 90 minutes depending on the quality and the quantity of the additive. After cooling the reaction mixture is neutralized with dilute hydrochloric acid and the polymer washed with distilled water. The product obtained is dehydrated with mixtures of acetone/water having increasing concentration and the air-dry substance obtained is dried in a drying oven at 105° C., thereafter milled for the fineness desired (<100 μm). So products marked with G to R are obtained.

For examining the products A to R the following comparative tests were performed.

Tablets were prepared with the following composition:

| | |
|---|---|
| product A to R | 2.5 weight % |
| microcrystalline cellulose (Avicel pH 102) | 94.0 weight % |
| talcum | 1.5 weight % |
| magnesium stearate | 2.0 weight % |

The tablets were pressed with to kind of pressure, i.e. with 0.1 MPa and 100 MPa, respectively. The disintegrating time and/or the water-absorption were determined on the tablets. The results are summarized in the following Tables.

TABLE I

| | Product A | Product B |
|---|---|---|
| | (according to Example 1) | |
| Water-absorption of tablets pressed with 0.1 MPa pressure (ml/g) | | |
| during 1 minute | 1.7 | 0.5 |
| during 10 minutes | 4.9 | 2.0 |
| final value | 5.5 | 5.5 |
| time until achieving the final value | 16 minutes | 60 minutes |
| Water-absorption of tablets pressed with 100 MPa pressure (ml/g) | | |
| during 1 minute | 0.5 | 0.2 |
| during 10 minutes | 3.7 | 1.0 |
| final value | 7.0 | 7.0 |
| time until achieving the final value | 28 minutes | 200 minutes |

TABLE II

| | Product C | Product D |
|---|---|---|
| | (according to Example 2) | |
| Water-absorption of tablets pressed with 0.1 MPa pressure (ml/g) | | |
| during 1 minute | 1.9 | 1.5 |
| during 10 minutes | 4.8 | 3.2 |
| final value | 5.1 | 5.5 |
| time until achieving the final value | 12 minutes | 33 minutes |
| Water-absorption of tablets pressed with 100 MPa pressure (ml/g) | | |
| during 1 minute | 0.8 | 0.7 |
| during 10 minutes | 4.3 | 3.0 |
| final value | 5.4 | 6.4 |
| time until achieving the final value | 15 minutes | 80 minutes |

TABLE III

| | Product E | Product F |
|---|---|---|
| | (according to Example 3) | |
| Water-absorption of tablets pressed with 0.1 MPa pressure (ml/g) | | |
| during 0.5 minute | 4.3 | 3.4 |
| during 1 minute | 6.0 | 4.4 |
| final value | 6.8 | 4.7 |
| time until achieving the final value | 1.33 minutes | 1.15 minutes |
| Water-absorption of tablets pressed with 100 MPa pressure (ml/g) | | |
| during 1 minute | 1.1 | 1.2 |
| during 5 minute | 4.0 | 3.4 |

TABLE III-continued

| | Product E | Product F |
|---|---|---|
| | (according to Example 3) | |
| final value | 7.0 | 4.2 |
| time until achieving the final value | 12 minutes | 8 minutes |

TABLE IV

| Alcohol-component | Mole alcohol component/ mole epichlorohydrin | Water-absorption at a pressure of 0.1 MPa (ml/g) | Water-absorption at a pressure of 100 MPa (ml/g) | Disintegrating time (minute) |
|---|---|---|---|---|
| Polyvinyl alcohol (product G) | 0.16* | 4.0 | 3.5 | 4 |
| — (product H) | — | 3.7 | 3.5 | 6 |
| n-propanol (product I) | 0.20 | 4.1 | 4.0 | 2.5 |
| n-butanol (product J) | 0.20 | 4.6 | 4.8 | 4 |
| n-octanol (product K) | 0.20 | 4.4 | 5.8 | 4 |
| ethylene glycol (product L) | 0.22 | 6.6 | 5.9 | 2.5 |
| propylene glycol (product M) | 0.30 | 4.9 | 5.4 | 2 |
| butylene glycol (product N) | 0.31 | 6.9 | 8.7 | 2 |
| triethylene glycol (product O) | 0.21 | 5.9 | 5.3 | 2 |
| tetraethylene glycol (product P) | 0.40 | 9.7 | 10.0 | 2 |
| glycerol (product R) | 0.15 | 5.0 | 5.2 | 2 |

*the mole ratio given for polyvinyl alcohol is calculated on vinyl alcohol units

We claim:

1. A cyclodextrin-epichlorohydrin polymer swelling quickly and to a great extent in water and containing as an alcohol additive a compound selected from the group consisting of n-octanol, ethylene glycol, propylene glycol, butylene glycol, triethylene glycol, and tetraethylene glycol.

2. The cyclodextrin-epichlorohydrin polymer defined in claim 1 which contains 2 to 8 moles of the alcohol additive per mole of cyclodextrin.

3. The cyclodextrin-epichlorohydrin polymer defined in claim 1 which contains n-octanol as the alcohol additive.

4. The cyclodextrin-epichlorohydrin polymer defined in claim 1 which contains ethylene glycol, propylene glycol, butylene glycol, triethylene glycol, or tetraethylene glycol as the alcohol additive.

5. The cyclodextrin-epichlorohydrin polymer defined in claim 1 which contains 0.2 moles of alcohol additive per mole of epichlorohydrin.

6. A process for preparing cyclodextrin-epichlorohydrin polymers swelling quickly and to a great extent in water which comprises the step of reacting cyclodextrin and epichlorohydrin in an aqueous alkaline medium wherein the cyclodextrin is reacted with 10 to 20 moles of an alkali hydroxide, 10 to 20 moles of epichlorohydrin and 2 to 8 moles of an alcohol additive selected from the group consisting of n-octanol, ethylene glycol, propylene glycol, butylene glycol, triethylene glycol, and tetraethylene glycol for each mole of cyclodextrin.

7. The process defined in claim 6 wherein n-octanol is the alcohol additive.

8. The process defined in claim 6 wherein ethylene glycol, propylene glycol, triethylene glycol, or tetraethylene glycol is the alcohol additive.

9. The process defined in claim 6 carried out in the presence of 10 to 15 moles of an organic solvent vaporizing at the reaction temperature.

10. The process defined in claim 6 wherein the organic solvent is ethylene glycol.

11. The process defined in claim 6 carried out in the presence of 8 to 12 moles of a high boiling organic solvent assuring a heterogeneous phase.

12. The process defined in claim 11 wherein the high boiling organic solvent is toluene.

13. The process defined in claim 6 wherein 0.2 moles of alcohol additive are employed per mole of epichlorohydrin.

* * * * *